(12) United States Patent
Davis et al.

(10) Patent No.: US 11,653,934 B2
(45) Date of Patent: *May 23, 2023

(54) SURGICAL INSTRUMENT AND METHOD

(71) Applicant: WARSAW ORTHOPEDIC INC., Warsaw, IN (US)

(72) Inventors: Darren Davis, Arlington, TN (US); Richard Hynes, Melbourne Beach, FL (US); Eric Lange, Collierville, TN (US); Anthony Melkent, Germantown, TN (US); Paul F. Wheeler, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 455 days.

This patent is subject to a terminal disclaimer.

(21) Appl. No.: 16/853,564

(22) Filed: Apr. 20, 2020

(65) Prior Publication Data

US 2020/0246026 A1 Aug. 6, 2020

Related U.S. Application Data

(60) Continuation of application No. 16/038,742, filed on Jul. 18, 2018, now Pat. No. 10,667,827, which is a division of application No. 14/640,189, filed on Mar. 6, 2015, now Pat. No. 10,080,571.

(51) Int. Cl.
*A61B 17/16* (2006.01)
*A61B 17/32* (2006.01)
*A61B 17/00* (2006.01)

(52) U.S. Cl.
CPC ...... *A61B 17/1671* (2013.01); *A61B 17/1659* (2013.01); *A61B 17/32002* (2013.01); *A61B 17/1644* (2013.01); *A61B 2017/00261* (2013.01); *A61B 2017/320032* (2013.01); *A61B 2217/005* (2013.01); *A61B 2217/007* (2013.01)

(58) Field of Classification Search
CPC ..... A61B 17/16; A61B 17/1671; A61B 17/32; A61B 17/32002
See application file for complete search history.

(56) References Cited

U.S. PATENT DOCUMENTS

| | | |
|---|---|---|
| 177,490 A | 5/1876 | Batflieu |
| 3,320,957 A | 5/1967 | Sokolik |
| 4,061,146 A | 12/1977 | Baehr et al. |
| 4,466,429 A | 8/1984 | Loscher et al. |
| 4,573,448 A | 3/1986 | Kambin |
| 4,603,694 A | 8/1986 | Wheeler |
| 4,646,738 A | 3/1987 | Trott |
| 4,711,607 A | 12/1987 | Wynosky et al. |
| 4,796,642 A | 1/1989 | Harris |
| 4,857,046 A | 8/1989 | Stevens et al. |
| 4,966,604 A | 10/1990 | Reiss |
| 5,030,201 A | 7/1991 | Palestrant |

(Continued)

*Primary Examiner* — Christopher J Beccia
(74) *Attorney, Agent, or Firm* — Sorell, Lenna & Schmidt, LLP

(57) ABSTRACT

A surgical instrument includes a first member defining an axis and including a cutting surface. A second member includes a cutting surface that is rotatable relative to the first member. A third member includes an outer surface. The cutting surface of the second member is rotatable relative to the outer surface to transfer the cut tissue along the axis. Systems and methods are disclosed.

20 Claims, 18 Drawing Sheets

(56) References Cited

U.S. PATENT DOCUMENTS

| | | |
|---|---|---|
| 5,071,424 A | 12/1991 | Reger |
| 5,074,871 A | 12/1991 | Groshong |
| 5,078,723 A | 1/1992 | Dance et al. |
| 5,100,423 A | 3/1992 | Fearnot |
| 5,108,404 A | 4/1992 | Scholten et al. |
| 5,156,610 A | 10/1992 | Reger |
| 5,158,564 A | 10/1992 | Schnepp-Pesch et al. |
| 5,178,625 A | 1/1993 | Groshong |
| 5,209,749 A | 5/1993 | Buelna |
| 5,211,651 A | 5/1993 | Reger et al. |
| 5,217,474 A | 6/1993 | Zacca et al. |
| 5,224,488 A | 7/1993 | Neuffer |
| 5,282,484 A | 2/1994 | Reger |
| 5,286,253 A | 2/1994 | Fucci |
| 5,312,427 A | 5/1994 | Shturman |
| 5,356,418 A | 10/1994 | Shturman |
| 5,360,432 A | 11/1994 | Shturman |
| 5,376,100 A | 12/1994 | Lefebvre |
| 5,383,884 A | 1/1995 | Summers |
| 5,411,514 A | 5/1995 | Fucci et al. |
| 5,415,656 A | 5/1995 | Tihon et al. |
| 5,437,630 A | 8/1995 | Daniel et al. |
| 5,527,326 A | 6/1996 | Hermann et al. |
| 5,529,580 A | 6/1996 | Kusunoki et al. |
| 5,556,408 A | 9/1996 | Farhat |
| 5,569,178 A | 10/1996 | Henley |
| 5,591,187 A | 1/1997 | Dekel |
| 5,693,011 A | 12/1997 | Onik |
| 5,695,513 A | 12/1997 | Johnson et al. |
| 5,772,676 A | 6/1998 | Cuschieri et al. |
| 5,836,947 A | 11/1998 | Fleischman et al. |
| 5,843,103 A | 12/1998 | Wulfman |
| 5,882,329 A | 3/1999 | Patterson et al. |
| 5,885,258 A | 3/1999 | Sachdeva et al. |
| 5,891,148 A | 4/1999 | Deckner |
| 5,891,153 A | 4/1999 | Peterson |
| 5,902,263 A | 5/1999 | Patterson et al. |
| 5,913,857 A | 6/1999 | Ritchart et al. |
| 5,941,869 A | 8/1999 | Patterson et al. |
| 5,954,737 A | 9/1999 | Lee |
| 5,964,716 A | 10/1999 | Gregoire et al. |
| 5,968,062 A | 10/1999 | Thomas et al. |
| 5,989,264 A | 11/1999 | Wright |
| 6,022,362 A | 2/2000 | Lee et al. |
| 6,068,642 A | 5/2000 | Johnson |
| 6,132,444 A | 10/2000 | Shturman et al. |
| 6,146,395 A | 11/2000 | Kanz et al. |
| 6,296,639 B1 | 10/2001 | Truckai et al. |
| 6,319,242 B1 | 11/2001 | Patterson et al. |
| 6,322,572 B1 | 11/2001 | Lee |
| 6,331,166 B1 | 12/2001 | Burbank et al. |
| 6,375,634 B1 | 4/2002 | Carroll |
| 6,379,346 B1 | 4/2002 | McIvor et al. |
| 6,423,081 B1 | 7/2002 | Lee et al. |
| 6,440,138 B1 | 8/2002 | Reiley et al. |
| 6,440,147 B1 | 8/2002 | Lee et al. |
| 6,454,775 B1 | 9/2002 | Demarais et al. |
| 6,471,702 B1 | 10/2002 | Goto |
| 6,494,890 B1 | 12/2002 | Shturman et al. |
| 6,540,747 B1 | 4/2003 | Marino |
| 6,554,799 B1 | 4/2003 | Hatamura et al. |
| 6,562,033 B2 | 5/2003 | Shah et al. |
| 6,575,970 B2 | 6/2003 | Quick |
| 6,592,559 B1 | 7/2003 | Pakter et al. |
| 6,596,005 B1 | 7/2003 | Kanz et al. |
| 6,638,288 B1 | 10/2003 | Shturman et al. |
| 6,659,105 B2 | 12/2003 | Burbank et al. |
| 6,660,014 B2 | 12/2003 | Demarais et al. |
| 6,663,626 B2 | 12/2003 | Truckai et al. |
| 6,673,023 B2 | 1/2004 | Pflueger |
| 6,676,658 B2 | 1/2004 | Burbank et al. |
| 6,679,886 B2 | 1/2004 | Weikel et al. |
| 6,689,145 B2 | 2/2004 | Lee et al. |
| 6,702,831 B2 | 3/2004 | Lee et al. |
| 6,726,685 B2 | 4/2004 | To et al. |
| 6,746,451 B2 | 6/2004 | Middleton et al. |
| 6,764,495 B2 | 7/2004 | Lee et al. |
| 6,780,175 B1 | 8/2004 | Sachdeva et al. |
| 6,796,989 B2 | 9/2004 | Uflacker |
| 6,824,551 B2 | 11/2004 | Trerotola |
| 6,849,080 B2 | 2/2005 | Lee et al. |
| 6,863,672 B2 | 3/2005 | Reiley et al. |
| 6,863,676 B2 | 3/2005 | Lee et al. |
| 6,923,813 B2 | 8/2005 | Phillips et al. |
| 6,945,977 B2 | 9/2005 | Demarais et al. |
| 6,958,044 B2 | 10/2005 | Burbank et al. |
| 6,989,011 B2 | 1/2006 | Paul et al. |
| 7,037,321 B2 | 5/2006 | Sachdeva et al. |
| 7,044,956 B2 | 5/2006 | Vetter et al. |
| 7,052,500 B2 | 5/2006 | Bashiri et al. |
| 7,114,501 B2 | 10/2006 | Johnson et al. |
| 7,122,011 B2 | 10/2006 | Clifford et al. |
| 7,192,430 B2 | 3/2007 | Truckai et al. |
| 7,198,626 B2 | 4/2007 | Lee et al. |
| 7,264,596 B2 | 9/2007 | Burbank et al. |
| 7,300,447 B2 | 11/2007 | Eliachar et al. |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,322,962 B2 | 1/2008 | Forrest et al. |
| 7,329,253 B2 | 2/2008 | Brounstein et al. |
| 7,329,267 B2 | 2/2008 | Weber |
| 7,335,198 B2 | 2/2008 | Eggers et al. |
| 7,338,495 B2 | 3/2008 | Adams |
| 7,357,801 B2 | 4/2008 | Burbank et al. |
| 7,476,226 B2 | 1/2009 | Weikel et al. |
| 7,503,920 B2 | 3/2009 | Siegal |
| 7,534,242 B2 | 5/2009 | Buehlmann et al. |
| 7,547,319 B2 | 6/2009 | Segal et al. |
| 7,578,819 B2 | 8/2009 | Bleich et al. |
| 7,591,790 B2 | 9/2009 | Pflueger et al. |
| 7,615,013 B2 | 11/2009 | Clifford et al. |
| 7,632,266 B2 | 12/2009 | Scopton et al. |
| 7,632,274 B2 | 12/2009 | Assell et al. |
| 7,637,927 B2 | 12/2009 | Hyde et al. |
| 7,641,664 B2 | 1/2010 | Pagano |
| 7,648,502 B2 | 1/2010 | Jacques |
| 7,666,202 B2 | 2/2010 | Prudnikov et al. |
| 7,682,378 B2 | 3/2010 | Truckai et al. |
| 10,080,571 B2* | 9/2018 | Davis ............... A61B 17/1659 |
| 10,667,827 B2* | 6/2020 | Davis ............... A61B 17/1671 |
| 2002/0016624 A1 | 2/2002 | Patterson et al. |
| 2002/0138021 A1 | 9/2002 | Pflueger |
| 2002/0138091 A1 | 9/2002 | Pflueger |
| 2003/0191474 A1 | 10/2003 | Cragg et al. |
| 2003/0208219 A1 | 11/2003 | Aznoian et al. |
| 2003/0233096 A1 | 12/2003 | Osorio et al. |
| 2004/0006355 A1 | 1/2004 | Vetter et al. |
| 2004/0024410 A1 | 2/2004 | Olson et al. |
| 2004/0059254 A1 | 3/2004 | Pflueger |
| 2004/0087956 A1 | 5/2004 | Weikel et al. |
| 2004/0092988 A1 | 5/2004 | Shaolian et al. |
| 2004/0162554 A1 | 8/2004 | Lee et al. |
| 2004/0167431 A1 | 8/2004 | Burbank et al. |
| 2004/0167432 A1 | 8/2004 | Burbank et al. |
| 2004/0267269 A1 | 12/2004 | Middleton et al. |
| 2005/0004492 A1 | 1/2005 | Burbank et al. |
| 2005/0043737 A1 | 2/2005 | Reiley et al. |
| 2005/0113836 A1 | 5/2005 | Lozier et al. |
| 2005/0137601 A1 | 6/2005 | Assell et al. |
| 2005/0182339 A1 | 8/2005 | Lee et al. |
| 2005/0197593 A1 | 9/2005 | Burbank et al. |
| 2005/0203527 A1 | 9/2005 | Garrison et al. |
| 2005/0209530 A1 | 9/2005 | Pflueger |
| 2005/0209610 A1 | 9/2005 | Carrison |
| 2005/0240193 A1 | 10/2005 | Layne et al. |
| 2005/0267502 A1 | 12/2005 | Hochman |
| 2006/0116689 A1 | 6/2006 | Albans et al. |
| 2006/0206118 A1 | 9/2006 | Kim et al. |
| 2006/0206136 A1 | 9/2006 | Sachdeva et al. |
| 2006/0229650 A1 | 10/2006 | Vetter et al. |
| 2006/0264957 A1 | 11/2006 | Cragg et al. |
| 2007/0055259 A1 | 3/2007 | Norton et al. |
| 2007/0055261 A1 | 3/2007 | Reiley et al. |

(56) References Cited

U.S. PATENT DOCUMENTS

| | | |
|---|---|---|
| 2007/0060935 A1* | 3/2007 | Schwardt ............... A61B 17/22 606/170 |
| 2007/0066977 A1 | 3/2007 | Assell et al. |
| 2007/0106246 A1 | 5/2007 | Modesitt et al. |
| 2007/0149990 A1 | 6/2007 | Palmer et al. |
| 2007/0162062 A1 | 7/2007 | Norton et al. |
| 2007/0173939 A1 | 7/2007 | Kim et al. |
| 2007/0197861 A1 | 8/2007 | Reiley et al. |
| 2007/0198020 A1 | 8/2007 | Reiley et al. |
| 2007/0203512 A1 | 8/2007 | Vetter et al. |
| 2007/0203513 A1 | 8/2007 | Vetter et al. |
| 2007/0239160 A1 | 10/2007 | Zipnick et al. |
| 2007/0255172 A1 | 11/2007 | Pflueger |
| 2007/0255277 A1 | 11/2007 | Nobis et al. |
| 2007/0255278 A1 | 11/2007 | Nobis et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0033465 A1 | 2/2008 | Schmitz et al. |
| 2008/0033466 A1 | 2/2008 | Assell et al. |
| 2008/0051812 A1 | 2/2008 | Schmitz et al. |
| 2008/0058588 A1 | 3/2008 | Emanuel |
| 2008/0058673 A1 | 3/2008 | Jansen et al. |
| 2008/0086157 A1 | 4/2008 | Stad et al. |
| 2008/0097436 A1 | 4/2008 | Culbert et al. |
| 2008/0114364 A1 | 5/2008 | Goldin et al. |
| 2008/0119846 A1 | 5/2008 | Rioux |
| 2008/0125783 A1* | 5/2008 | Perez-Cruet ..... A61B 17/32002 606/82 |
| 2008/0154275 A1 | 6/2008 | Assell et al. |
| 2008/0188879 A1 | 8/2008 | Vakharia et al. |
| 2008/0208255 A1 | 8/2008 | Siegal |
| 2008/0221505 A1 | 9/2008 | Betts |
| 2008/0228192 A1 | 9/2008 | Beyar et al. |
| 2008/0249552 A1 | 10/2008 | Eliachar et al. |
| 2008/0269760 A1 | 10/2008 | Reiley et al. |
| 2008/0281323 A1 | 11/2008 | Burbank et al. |
| 2008/0281364 A1 | 11/2008 | Chirico et al. |
| 2008/0294166 A1 | 11/2008 | Goldin et al. |
| 2008/0294167 A1 | 11/2008 | Schumacher et al. |
| 2009/0043259 A1 | 2/2009 | Hardin, Jr. et al. |
| 2009/0062872 A1 | 3/2009 | Chin et al. |
| 2009/0149877 A1 | 6/2009 | Hanson et al. |
| 2009/0292323 A1 | 11/2009 | Chirico et al. |
| 2009/0299219 A1 | 12/2009 | Pflueger |
| 2010/0036402 A1 | 2/2010 | Hanson et al. |
| 2010/0076476 A1 | 3/2010 | To et al. |
| 2010/0121361 A1 | 5/2010 | Plowe et al. |
| 2010/0125272 A1 | 5/2010 | Scopton et al. |

\* cited by examiner

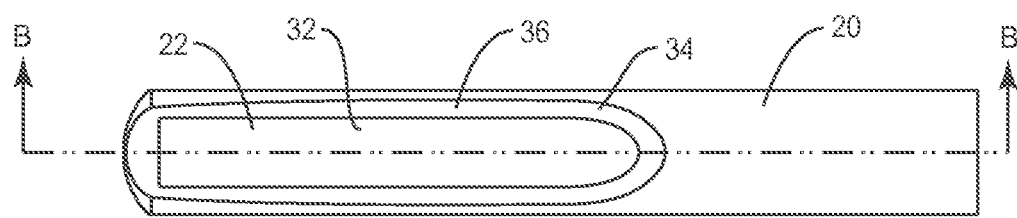
FIG. 4
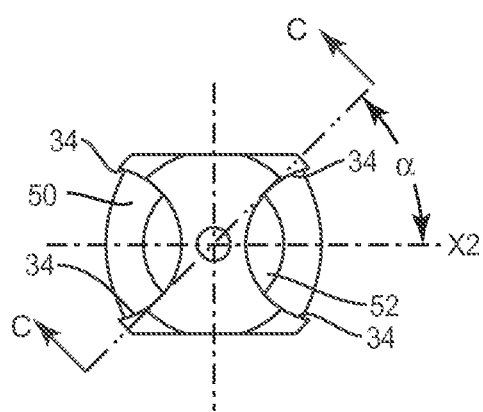 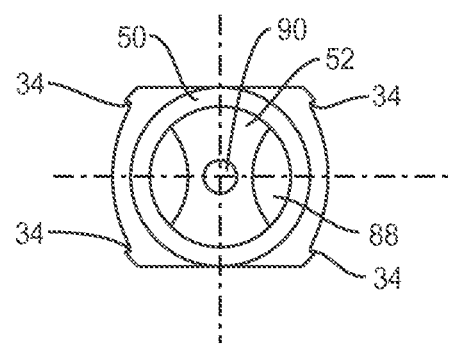
FIG. 5  FIG. 6

SURGICAL INSTRUMENT AND METHOD

CROSS-REFERENCE TO RELATED APPLICATION

This application is a continuation of U.S. patent application Ser. No. 16/038,742, which is a division of U.S. patent application Ser. No. 14/640,189, filed on Mar. 6, 2015, now U.S. Pat. No. 10,080,571. These applications are hereby incorporated herein by reference, in their entireties.

TECHNICAL FIELD

The present disclosure generally relates to medical devices for the treatment of musculoskeletal disorders, and more particularly to a surgical system for preparation of a surgical site and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior art technologies.

SUMMARY

In one embodiment, a surgical instrument is provided. The surgical instrument includes a first member defining an axis and including a cutting surface. A second member includes a cutting surface that is rotatable relative to the first member. A third member includes an outer surface. The cutting surface of the second member is rotatable relative to the outer surface to transfer the cut tissue along the axis. Systems and methods of use are disclosed.

BRIEF DESCRIPTION OF THE DRAWINGS

The present disclosure will become more readily apparent from the specific description accompanied by the following drawings, in which:

FIG. 4 is a side view of components of the system shown in FIG. 1;

FIG. 5 is an end view of components of the system shown in FIG. 1;

FIG. 6 is an end view of components of the system shown in FIG. 1;

DETAILED DESCRIPTION

Figure 1:
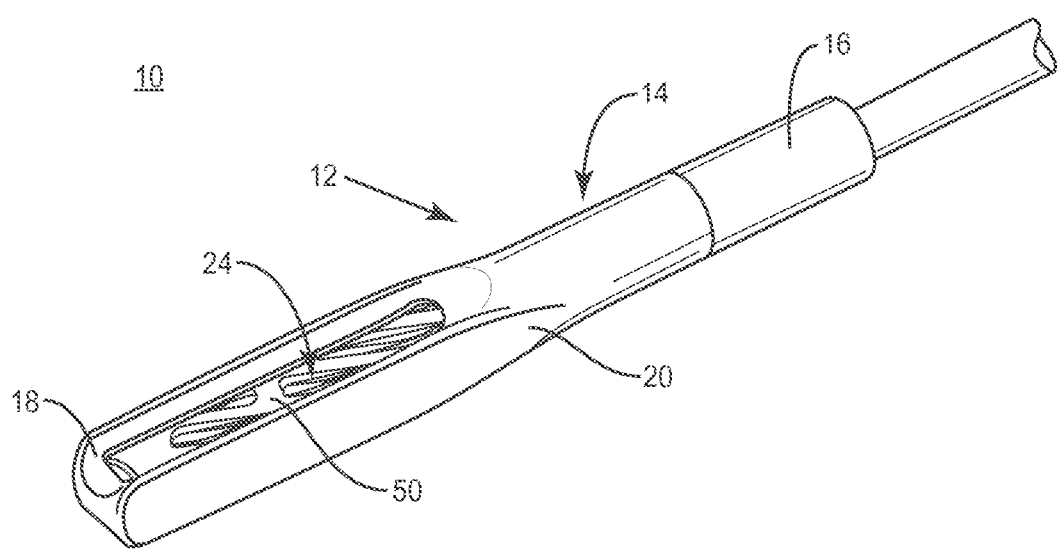
FIG. 1 is a perspective view of components of one embodiment of a surgical system in accordance with the principles of the present disclosure.
Figure 2:
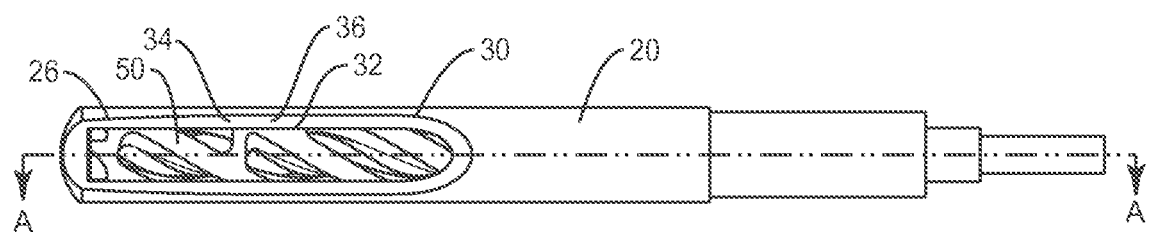
FIG. 2 is a side view of the components shown in FIG. 1.

The exemplary embodiments of the surgical system and related methods of use disclosed are discussed in terms of medical devices for the treatment of musculoskeletal disorders and more particularly, in terms of a surgical system for preparation of a surgical site and a method for treating a spine.

In one embodiment, the surgical system includes a surgical instrument, such as, for example, a disc preparation instrument. In some embodiments, the surgical instrument includes a manual cutter housing disposed about an internal rotating cutter. In some embodiments, the surgical system includes a disc preparation device with a combination of an outer paddle scraper structure having two or more blades or openings between the blades and an internal rotating auger and/or suction mechanism for conveying disc debris into the instrument and away from the surgical site.

In some embodiments, the surgical system includes a surgical instrument including a rotating cutter housing that provides a rigid protective cover configured to cover the rotating cutter blade. In some embodiments, the cutter housing includes at least two openings with four sharp edges to facilitate cutting of peripheral material when rotated. In some embodiments, the peripheral material is processed via the internal cutting and grinding mechanism. In some embodiments, the surgical instrument includes a housing configured to incorporate one, two, and/or multiple openings to facilitate accessibility to the internal cutting and grinding mechanism. In some embodiments, the surgical instrument includes a rotating cutter mechanism disposed with the rotating cutter housing for cutting and/or macerating disc material. In some embodiments, the surgical instrument includes suction to facilitate material removal. In one embodiment, the surgical instrument includes a navigation device to facilitate positioning and/or tracking of components of the surgical system.

In some embodiments, the surgical instrument is configured to be surgically inserted into a space between vertebral bodies to facilitate cutting and removing tissue and bone to create a space or pathway for fusion or motion implants. In some embodiments, the surgical instrument includes a rotating cutter housing, a rotating cutter, a stationary auger, a rotating grinder, and an irrigation and/or debris removal tube.

In one embodiment, the surgical instrument includes a rotating cutter having a circumferential helical cutting geometry that is configured to create shear against an inside portion of the housing. In some embodiments, the helical shape can be either a right hand or left hand cutter feature. In some embodiments, the surgical instrument includes a cannulated rotatable cutter to facilitate mating with a stationary auger. In some embodiments, the surgical instrument includes a rotor/stator combination to facilitate high shear to process cut material into a smaller particle size. In some embodiments, the helical shape causes cut debris to channel inside the stationary auger and is forced towards a rotating grinder. In some embodiments, the surgical instrument includes a rotating cutter having an end configured with a cutting geometry to facilitate insertion. In some embodiments, the surgical instrument includes irrigation surfaces that facilitate irrigation to enter the auger channels to mix with debris to provide a transfer mixture, and create a hydraulic bearing surface between moving parts of the cutter.

In one embodiment, the surgical instrument includes a stationary auger member that includes a rotational pitch opposite of the cutter to create a force along auger channels to transfer cut material towards a rotating grinder. In some embodiments, the auger is cannulated to facilitate irrigation to transfer to a tip of the rotating cutter. In some embodiments, the surgical instrument includes a rotating cutter having irrigation and/or a hydraulic bearing surface and irrigation holes.

In one embodiment, the surgical instrument includes a rotating grinder that includes pathways to facilitate irrigation around a peripheral surface of the rotating cutter to transfer to the cannulated stationary auger member. In one embodiment, the rotating grinder includes a grinding surface and a debris portal. In one embodiment, the rotating grinder includes an irrigation channel and debris removal oriented in a selected direction. In some embodiments, the surgical instrument includes a grinding surface configured to cause a high shear with the stationary auger member as material is forced into debris portals.

In one embodiment, the surgical instrument includes debris irrigation and suction. In one embodiment, the surgical instrument includes a manual blade with a spinning cutter having an internal stationary auger. In some embodiments, the surgical instrument includes an irrigation port disposed in a handle and a suction connection in the handle. In one embodiment, the manual blade includes a pair of cutting elements. In one embodiment, the manual blade includes four cutting elements oriented in a cruciate configuration. In one embodiment, the surgical instrument includes scrape blades and rotating blades. In one embodiment, the surgical instrument is employed with a method such that a surgeon cuts away disc and endplate tissue with the manual blade by manually rotating and/or scraping the tissue. In some embodiments, the method includes the step of moving tissue debris into ports between the manual blades.

In some embodiments, the surgical instrument includes an auger having a central cannula configured for disposal of a piston. In some embodiments, the piston is disposed with the central cannula and within a rotating blade disposed thereabout. In some embodiments, the piston translates relative to the auger in a first axial direction and/or in a second axial direction to move tissue debris. In some embodiments, the piston comprises a compactor to engage and move tissue debris for removal of the tissue debris from the auger and/or to facilitate grinding and cutting of tissue.

In some embodiments, components of the surgical instrument have a central cannula configured for disposal of an illumination device. In some embodiments, the illumination device includes a fiber-optic light cable. In some embodiments, components of the surgical instrument include a fiber-optic light and a camera mounted with an outer housing and/or a stationary shaft, as described herein. In some embodiments, the camera includes a miniature camera.

In some embodiments, the surgical instrument includes an auger comprising two or more counter rotating internal blades. In some embodiments, the blades are co-axially disposed and comprise alternate diameters, increasing or decreasing. In some embodiments, the blades are separate and disposed in a serial configuration. In some embodiments, the blades may rotate in the same or different directions.

In some embodiments, the surgical instrument includes a manual cutter housing that collects tissue debris, as described herein, and arrests movement of the components of the surgical system to close and seal the surgical instrument. In some embodiments, this configuration increases a suction force to facilitate removal of tissue debris from the cutters and/or blades. In some embodiments, the components of the surgical instrument can be heated and/or cooled to facilitate processing of tissue, as described herein. In some embodiments the surgical instrument includes an inner blade, such as, for example, the stationary shaft, having a heating or cooling element that heats or freezes tissue, such as, for example, intervertebral disc tissue and an outer blade, such as, for example, the rotatable cutter, having an insulating element disposed about the inner blade. The heating or cooling element can be electrically connected to a power source.

In some embodiments, the cutting surfaces or blades of the components of the surgical instrument, as described herein, can include, such as, for example, diamonds, spikes and/or sandpaper. In some embodiments, the surgical system includes a diverting filter connected to the surgical instrument and configured to bifurcate tissue debris into a plurality of portions of the filter. In some embodiments, the filter includes at least one portion that facilitates trapping and collecting bone.

In some embodiments, the surgical system includes a device configured to inject a bio-material, such as, for example, a polymer, cement, or stiffener into intervertebral disc tissue. In some embodiments, the bio-material is injected with tissue to quick set at the time of surgery or prepared and introduced before the surgery. In some embodiments, the surgical system includes a bio-material, such as, for example, a discogram injection to stiffen intervertebral disc tissue and increase cutting efficiency. In some embodiments, the surgical system is employed with a method such that intervertebral disc tissue is heated and/or bio-frozen prior to cutting to alter the disc material characteristics and to facilitate cutting.

In one embodiment, one or all of the components of the surgical system are disposable, peel-pack, pre-packed sterile devices that can be used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context dearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-25, there are illustrated components of a surgical system 10 including a surgical instrument 12.

The components of surgical system 10 can be fabricated from biologically acceptable materials suitable for medical applications, including metals, synthetic polymers, ceramics and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including surgical instrument 12 can be employed, for example, with mini-open and open surgical techniques to prepare a surgical site including tissue in connection with a surgical procedure for delivery and introduction of instrumentation and/or an implant, such as, for example, an intervertebral implant, at a surgical site within a body of a patient, for example, a section of a spine. In one embodiment, surgical system 10 may be employed with surgical procedures, such as, for example, corpectomy and discectomy, which include fusion and/or fixation treatments that employ implants.

Surgical instrument 12 includes a member, such as, for example, a body 14 that extends between an end 16 and an end 18. Body defines an axis X1 and includes a housing 20. In some embodiments, housing 20 may have cross section configurations, such as, for example, oval, cylindrical, triangular, square, polygonal, irregular, uniform, non-uniform, offset, staggered, undulating, arcuate, variable and/or tapered. Housing 20 includes an inner surface 21 that defines a cavity, such as, for example, a channel 22. Channel 22 is configured for disposal of a member, such as, for example, an auger 24, as described herein. In some embodiments, channel 22 may have various cross section configurations, such as, for example, circular, cylindrical, oval, oblong, triangular, rectangular, square, polygonal, irregular, uniform, non-uniform, variable, tubular and/or tapered. In some embodiments, housing 20 is configured to provide a rigid protective cover for auger 24.

Housing 20 includes a wall 26 disposed about auger 24. Wall 26 includes a thickness and a surface 30. Surface 30 defines spaced openings 32 extending through the thickness of wall 26. Wall 26 includes a cutting surface 34 that is disposed about openings 32. Wall 26 has a tapered cross section configuration that extends to cutting surface 34, which includes blades 36. Blades 36 are configured to disrupt, scrape, cut and/or remove tissue from a surgical site. In some embodiments, housing 20 may include one or a plurality of spaced openings.

Manipulation including rotation, translation and/or angulation of housing 20 causes blades 36 to disrupt, scrape, cut and/or remove tissue at a surgical site and guide tissue into channel 22. In some embodiments, blades 36 are configured for disposal between vertebral bodies to disrupt, scrape, cut and/or remove tissue, such as, for example, intervertebral disc tissue and/or vertebral endplate tissue to create a cavity, space and/or pathway at a surgical site including a targeted portion of an anatomy for delivery, introduction and/or implantation of a spinal implant. In some embodiments, cutting surface 34 is disposed at an angle $\alpha$ relative to an axis X2 of housing 20 to direct cut tissue into channel 22. In some embodiments, angle $\alpha$ is 45 degrees. In some embodiments, angle $\alpha$ may include an angle in a range of 0 through 180 degrees. In some embodiments, cutting surface 34 may be disposed at alternate orientations relative to housing 20, such as, for example, transverse, perpendicular and/or other angular orientations such as acute or obtuse, co-axial and/or may be offset or staggered.

Auger 24 is configured for disposal in channel 22. Auger 24 includes a member, such as, for example, a rotatable cutter 50 and a member, such as, for example, a stationary shaft 52. Cutter 50 extends between an end 54 and an end 56. Cutter 50 extends along axis X1 when disposed in channel 22. Cutter 50 is tubular in configuration. In some embodiments, cutter 50 may have cross section configurations, such as, for example, oval, cylindrical, triangular, square, polygonal, irregular, uniform, non-uniform, offset, staggered, undulating, arcuate, variable and/or tapered.

Cutter 50 includes a surface 58 that defines a plurality of spaced cutting flutes 60. Cutting flutes 60 are spaced along cutter 50 and form helical blades 62 extending along a length of cutter 50. Helical blades 62 are disposed at a rotational pitch R1. In some embodiments, surface 58 includes a scaffold and/or network of blades. In some embodiments, blades 62 may be disposed at alternate relative orientations, such as, for example, parallel, transverse and/or other angular orientations such as acute or obtuse, co-axial and/or may be offset or staggered. Blades 62 are configured for rotation within housing 20 and about shaft 52 to disrupt, scrape, cut, shear and/or macerate tissue and/or transfer and/or convey tissue along shaft 52, as described herein.

Figure 3:
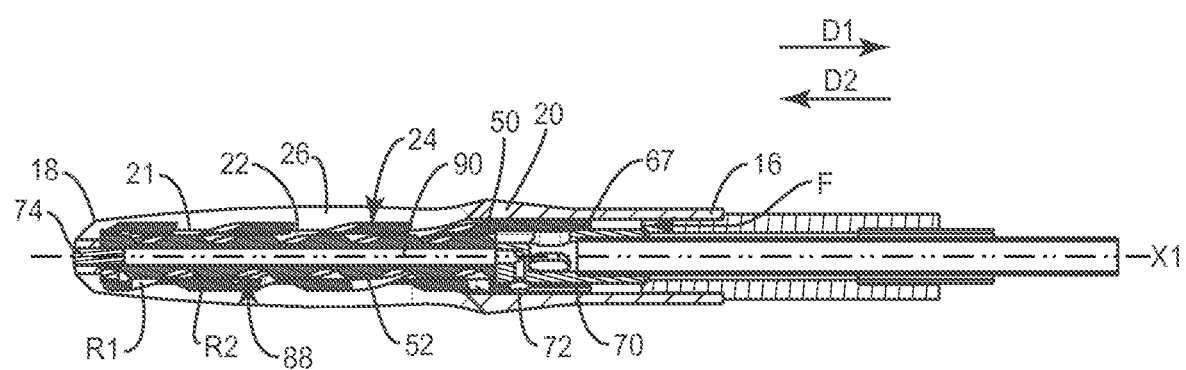
FIG. 3 is a cross section view taken along lines A-A shown in FIG. 2.
Figure 7:
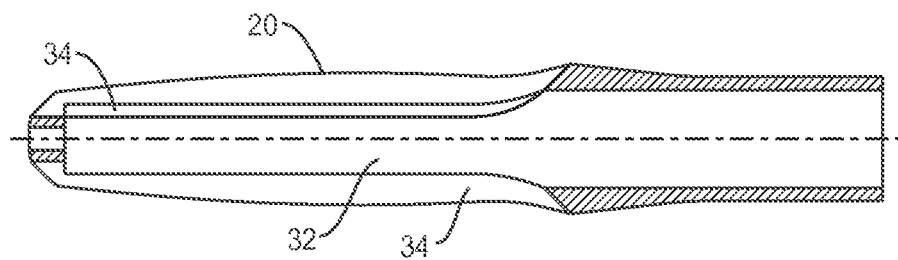
FIG. 7 is a cross section view taken along lines B-B shown in FIG. 4.
Figure 8:
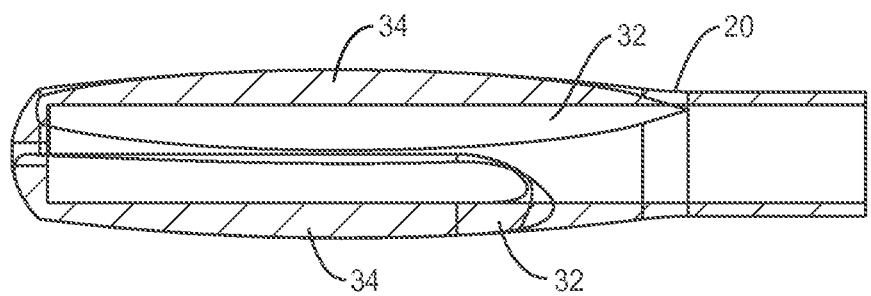
FIG. 8 is a cross section view taken along lines C-C shown in FIG. 5.

Cutter 50 includes an inner surface 64 that defines an interior cavity 66. Cavity 66 is configured for disposal of shaft 52 within housing 20, as described herein. Cutter 50 is configured for rotation relative to shaft 52 to transfer tissue along a first direction, such as, for example, a direction D1 along axis X1, as shown in FIG. 3 and described herein. In some embodiments, blades 62 rotate relative to shaft 52 within housing 20 to disrupt, scrape, cut, shear and/or macerate cut tissue from blades 36 into a smaller particle size for removal a surgical site. In some embodiments, blades 62 rotate such that tissue disposed adjacent and/or between cutter 50 and shaft 52 is transferred and/or conveyed in direction D1 due to fluid transfer forces created between the helical configurations of cutter 50 and shaft 52. The tissue is transferred and/or conveyed towards a member, such as, for example, a grinder 100 for removal from a surgical site, as described herein. In some embodiments, auger 24 comprises two or more counter rotating internal blades, similar to cutter 50. In some embodiments, the blades are co-axially disposed and comprise alternate diameters, increasing or decreasing. In some embodiments, the blades are separate and disposed in a serial configuration. In some embodiments, the blades may rotate in the same or different directions.

End 54 includes a portion 67 having a surface 68 and a surface 69. Surface 68 defines an opening 70 configured for disposal of a portion of grinder 100. Surface 69 includes a cavity, such as, for example, a groove 71. Groove 71 is in communication with a fluid F supplied from an irrigation port, as described herein. Fluid F flows along groove 71 through openings, such as, for example, irrigation holes 72. Holes 72 are configured to direct fluid F through grinder 100 and into shaft 52, as described herein. In some embodiments, fluid F passes along groove 70 and provides a hydraulic bearing surface with grinder 100 to facilitate rotation of cutter 50 and prevent wear, overheating and/or damage during operation of the components of surgical instrument 12.

Shaft 52 extends between an end 80 and an end 82 along axis X1 when disposed in housing 20. Shaft 52 is configured for disposal with cavity 66. Shaft 52 is fixed with housing 20 by a protrusion, such as, for example, a flange 74. Flange 74 is fixedly attached with shaft 52 to resist and/or prevent rotation. In some embodiments, shaft 52 may have cross section configurations, such as, for example, oval, cylindrical, triangular, square, polygonal, irregular, uniform, non-uniform, offset, staggered, undulating, arcuate, variable and/or tapered.

Figure 37:
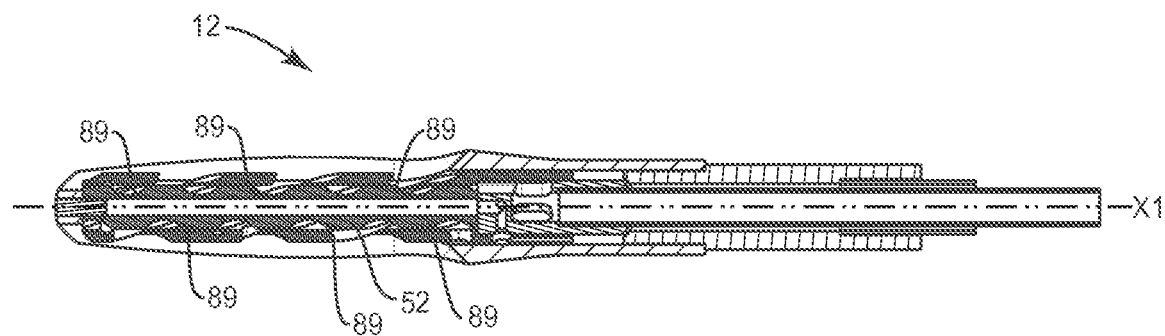
FIG. 37 is a cross section view of components of one embodiment of a surgical system in accordance with the principles of the present disclosure.

Shaft 52 includes a surface 84 that defines a helical surface 86. Helical surface 86 is disposed in an alternate orientation relative to helical blades 62. Helical surface 86 includes a rotational pitch R2 that is alternative to rotational pitch R1 to create a dynamic fluid transfer and/or shear force or pressure to transfer and/or convey tissue from a surgical site in direction D1. Helical blades 62 and helical surface 86 form a transfer channel 88 therebetween configured to direct cut tissue along axis X1 towards grinder 100 in direction D1. The dynamic fluid transfer and/or shear force created by rotation of cutter 50 relative to shaft 52 and between helical blades 62 and helical surface 86 direct fluid flow and cut tissue within transfer channel 88. In some embodiments, surface 58 and/or surface 84 may comprise alternate configurations, such as, for example, grooved, channeled, undulating, even, uniform, non-uniform, offset, staggered, textured and/or tapered to facilitate directional flow of fluid F. In one embodiment, as shown in FIG. 37, shaft 52 includes fiber-optic light cable 89 disposed and/or helically wound through a surface of shaft 52. Light-cable 89 illuminates a surgical site. In some embodiments, an illumination device may be mounted with various components of surgical instrument 12. In one embodiment, a miniature camera (not shown) can be mounted with various components of surgical instrument 12 to facilitate imaging of the surgical site.

Shaft 52 is cannulated to define a passageway 90 configured for transfer of fluid F in a direction, such as, for example, a direction D2. Passageway 90 is in communication with irrigation holes 72 via channels 118, 120, 122, as described herein. Surface 84 at end 82 defines at least one opening 92 configured to direct fluid flow F out of passageway 90 into transfer channel 88. The force of fluid flow F travelling through passageway 90 causes fluid flow F to exit passageway 90 through openings 92. Fluid F is expelled from passageway 90 and is utilized to facilitate transfer of tissue along transfer channel 88 in direction D1 to grinder 100. Movement of fluid F through openings 92 creates a hydraulic bearing surface at ends 82, 56 between cutter 50 and shaft 52 to facilitate rotation of cutter 50 and prevent wear, overheating and/or damage during operation of the components of surgical instrument 12.

Grinder 100 extends between an end 102 and an end 104. End 104 is configured for disposal in portion 67 of cutter 50. Grinder 100 includes a surface 106 that defines a cutting surface, such as, for example, a plurality of arcuate cutting blades 108 configured to cut, shear and/or macerate cut tissue from transfer channel 88 into a smaller particle size for removal from a surgical site. Cutting blades 108 form openings 110. Grinder 100 includes a surface 112 that defines a debris reservoir 114. Openings 110 are in communication with debris reservoir 114 such that the tissue that passes through openings 110 is transferred and/or conveyed into debris reservoir 114 for removal by a vacuum source attached with housing 20. In some embodiments, the cutting surfaces described herein may include blades, serrations, tines, sharpened surfaces and/or edges.

Grinder 100 includes a surface 116 that defines a fluid flow pathway, such as, for example, a series of channels, such as, for example, channels 118, 120, 122. Channels 118, 120, 122 communicate at junction 124 to facilitate the flow of fluid F through grinder 100 into passageway 90. In some embodiments, channels 118, 120, 122 may be disposed at alternate relative orientations, such as, for example, transverse, perpendicular and/or other angular orientations such as acute or obtuse, co-axial and/or may be offset or staggered.

Channels 118, 120, 122 are each configured for alignment with holes 72 during rotation to receive fluid F. Junction 124 is oriented in communication with passageway 90. Channels 118, 120, 122 are configured to receive fluid flow F from holes 72 and direct fluid flow F to junction 124 into passageway 90 of shaft 52, as described herein, to direct fluid F in direction D2 into passageway 90.

Grinder 100 is configured for rotation relative to shaft 52 between an open, fluid communication position such that openings 110 are aligned with transfer channel 88 to facilitate passage of cut tissue from transfer channel 88 to debris reservoir 114 and a closed, non-communicating position such that surface 106 prevents passage of cut tissue from transfer channel 88 into debris reservoir 114. As grinder 100 rotates between the open and closed positions of openings 110, blades 108 shear tissue with shaft 52 to cut, shear and/or macerate cut tissue from transfer channel 88 into a smaller particle size for removal from a surgical site. Cut tissue is transferred and/or conveyed with fluid F in direction D1. In some embodiments, the open position of grinder 100 comprises a range of alignment of openings 110 with transfer channel 88 including a fully open position of openings 110 through gradual closing of openings 110 during rotation to a completely closed orientation such that surface 106 completely blocks openings 110.

An irrigation port is configured to deliver fluid F into surgical instrument 12, through holes 72, through channels 118, 120, 122 and into passageway 90. The force of fluid flow F directs cut tissue through transfer channel 88 to grinder 100. Fluid F mixed with tissue is transferred into debris reservoir 114 for removal via the vacuum source connected with surgical instrument 12. In some embodiments, surgical system 10 includes a diverting filter (not shown) connected to surgical instrument 12 and configured to bifurcate tissue debris into a plurality of portions of the filter. In some embodiments, the filter includes at least one portion that facilitates trapping and collecting bone.

Figure 26:
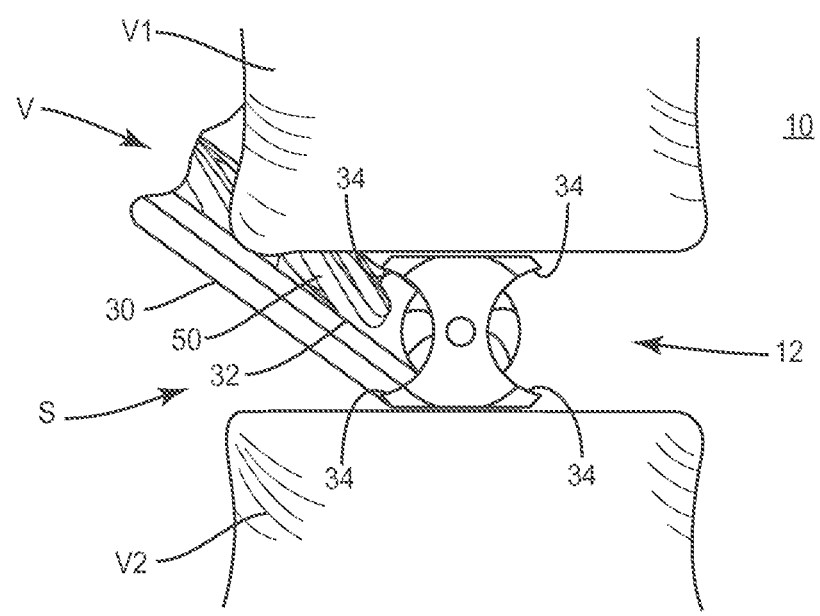
FIG. 26 is a perspective view of components of one embodiment of a surgical system in accordance with the principles of the present disclosure disposed with vertebrae.
Figure 27:
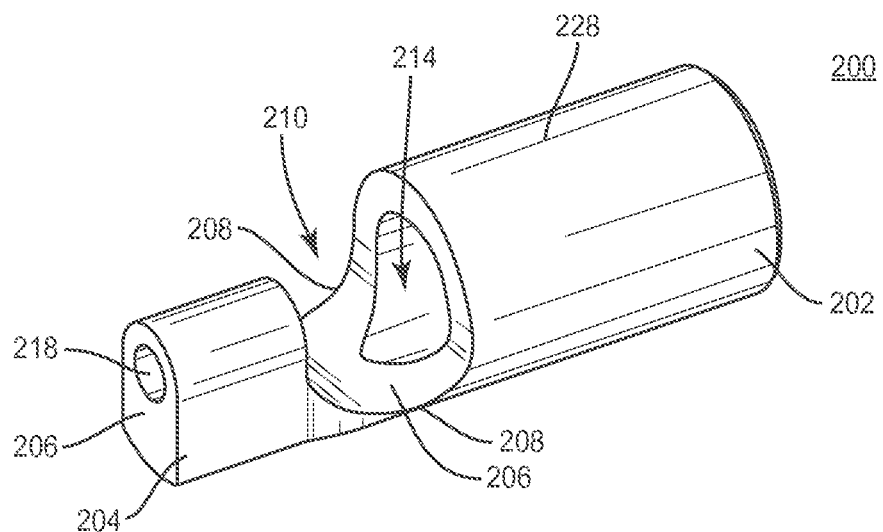
FIG. 27 is a perspective view of components of one embodiment of a surgical system in accordance with the principles of the present disclosure.
Figure 28:
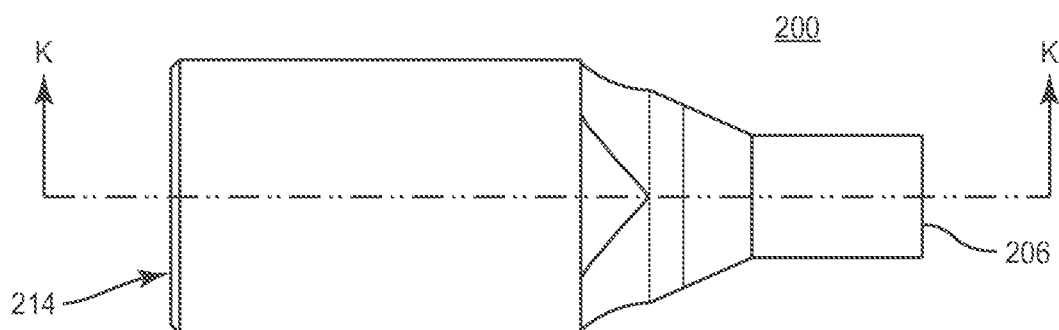
FIG. 28 is a side view of the components shown in FIG. 27.
Figure 29:
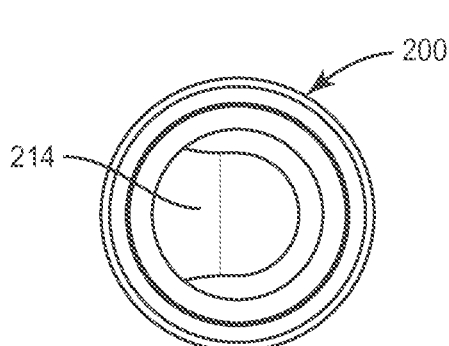
FIG. 29 is an end view of the components shown in FIG. 27.
Figure 30:
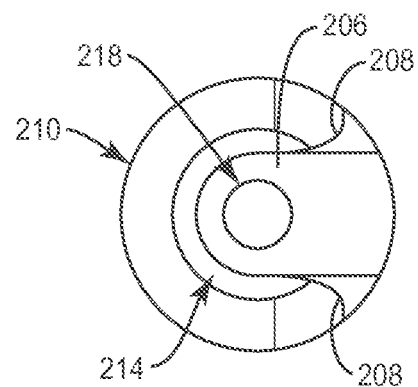
FIG. 30 is an end view of the components shown in FIG. 27.
Figure 31:
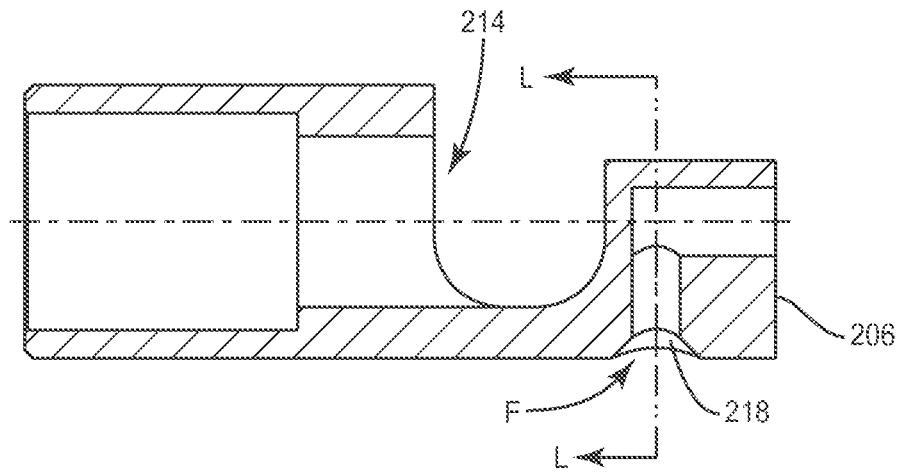
FIG. 31 is a cross section view taken along lines K-K of FIG. 28.
Figure 32:
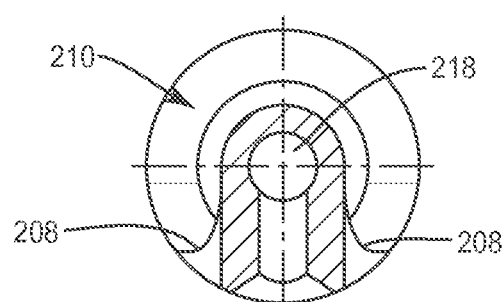
FIG. 32 is a cross section view taken along lines L-L of FIG. 28.

In assembly, operation and use, as shown in FIG. 26, surgical system 10 is employed to treat an affected section of vertebrae V. A medical practitioner obtains access to a surgical site including vertebrae V in any appropriate manner, such as through incision and retraction of tissues. The components of surgical system 10 including surgical instrument 12 are employed to augment a surgical treatment. Surgical instrument 12 can be delivered to a surgical site as a pre-assembled device or can be assembled in situ. Surgical system 10 may be may be completely or partially revised, removed or replaced.

Surgical system 10 may be used with surgical methods or techniques including open surgery, mini-open surgery, minimally invasive surgery and percutaneous surgical implantation, whereby vertebrae V is accessed through a mini-incision, or sleeve that provides a protected passageway to the area. Once access to the surgical site is obtained, a surgical treatment, for example, corpectomy and/or discectomy, can be performed for treating a spine disorder. A diseased and/or damaged portion of vertebrae V between and/or including vertebra V1, V2, and diseased and/or damaged intervertebral discs and tissue are removed to create a vertebral space S.

Surgical instrument 12 is delivered to the surgical site including vertebrae V and inserted with space S. Housing 20 is manipulated including rotation, translation and/or angulation of housing 20 for engagement with vertebral tissue, including but not limited to intervertebral tissue, endplate tissue and bone, adjacent space S causing blades 36 to disrupt, scrape, cut and/or remove tissue from the surgical site and guide tissue into channel 22, as described herein. An actuator, such as, for example, an electric motor is connected with surgical instrument 12 to actuate rotation of cutter 50 and grinder 100 relative to shaft 52.

A source of fluid F is connected to the irrigation port of surgical instrument 12 to establish fluid flow in directions D1, D2, as described herein. Cutter 50 rotates relative to shaft 52 such that blades 62 rotate to disrupt, scrape, cut, shear and/or macerate cut tissue from blades 36 into a smaller particle size for removal the surgical site.

Blades 62 rotate such that tissue disposed adjacent and/or between cutter 50 and shaft 52 is transferred and/or conveyed in direction D1 due to fluid transfer forces created between the helical configurations of cutter 50 and shaft 52. The dynamic fluid transfer and/or shear force created by rotation of cutter 50 relative to shaft 52 and between helical blades 62 and helical surface 86 direct fluid F and cut tissue within transfer channel 88, as described herein.

The tissue is transferred and/or conveyed to grinder 100 for removal from the surgical site. As grinder 100 rotates between the open and closed positions of openings 110, as described herein, blades 108 shear tissue with shaft 52 to cut, shear and/or macerate cut tissue from transfer channel 88 into a smaller particle size for removal from the surgical site. Cut tissue is transferred and/or conveyed with fluid F in direction D1. The force of fluid F directs cut tissue through transfer channel 88 to grinder 100. Fluid F mixed with tissue is transferred into debris reservoir 114 for removal via the vacuum source connected with surgical instrument 12.

In some embodiments, surgical system 10 can include one or more surgical instruments for use with surgical instrument 12, such as, for example, drivers, inserters, extenders, reducers, spreaders, distractors, blades, retractors, clamps, forceps, elevators and drills, which may be alternately sized and dimensioned, and arranged as a kit.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae V. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of surgical system 10 are removed and the incision is closed. The components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

Figure 9:
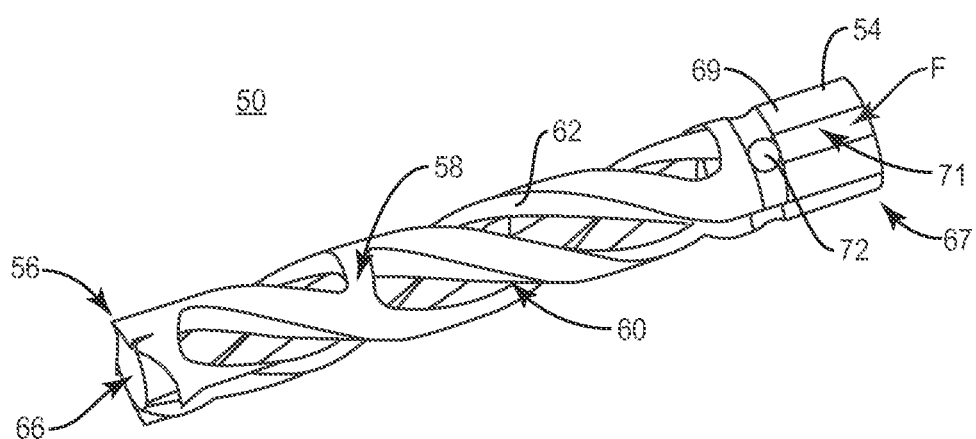
FIG. 9 is a perspective view of components of the system shown in FIG. 1.
Figure 10:
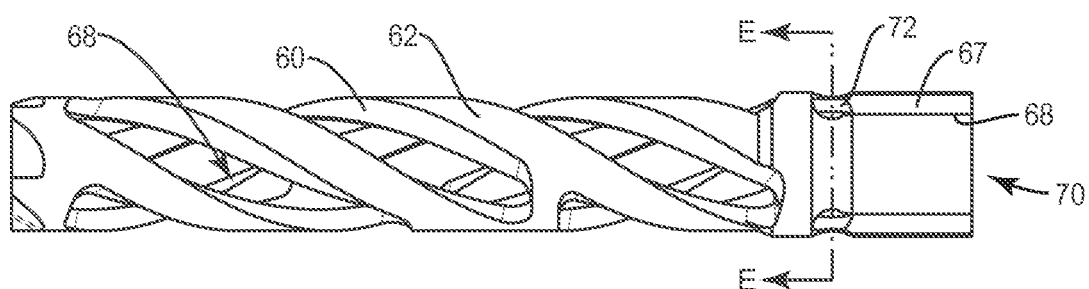
FIG. 10 is a side view of components of the system shown in FIG. 1.
Figure 11:
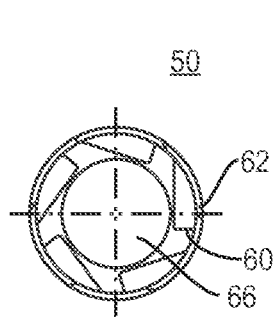
FIG. 11 is an end view of the components shown in FIG. 10.
Figure 12:
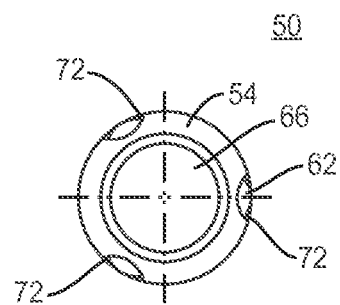
FIG. 12 is an end view of the components shown in FIG. 10.
Figure 13:
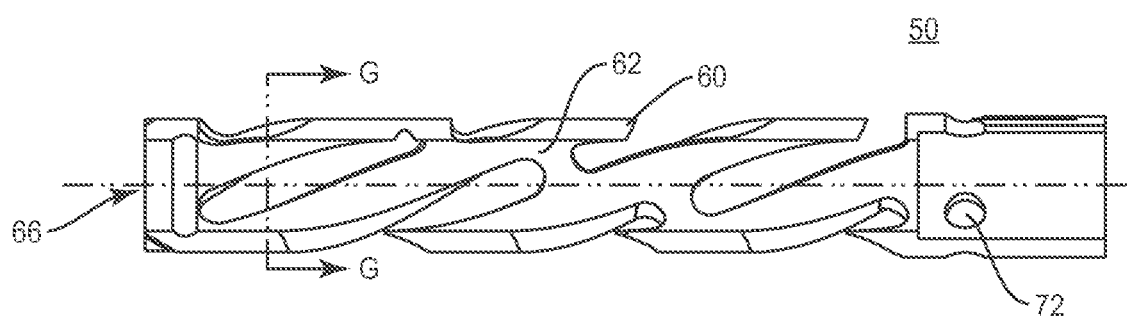
FIG. 13 is a cross section view of components of the system shown in FIG. 1.
Figure 14:
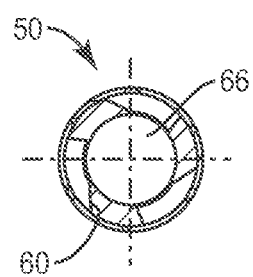
FIG. 14 is a cross section view taken along lines G-G shown in FIG. 13.
Figure 15:
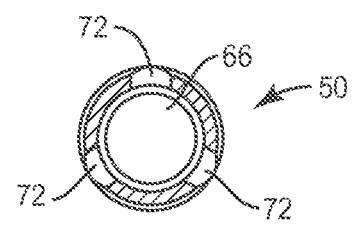
FIG. 15 is a cross section view taken along lines E-E shown in FIG. 10.
Figure 16:
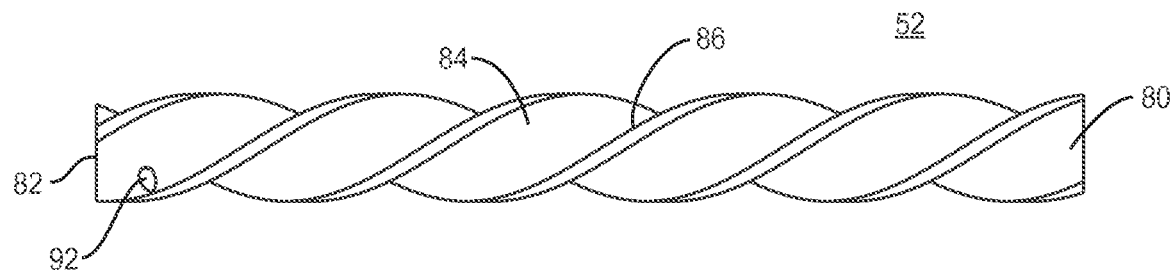
FIG. 16 is a side view of components of the system shown in FIG. 1.
Figure 17:
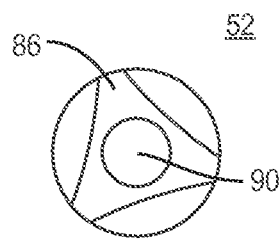
FIG. 17 is an end view of the components shown in FIG. 16.
Figure 18:
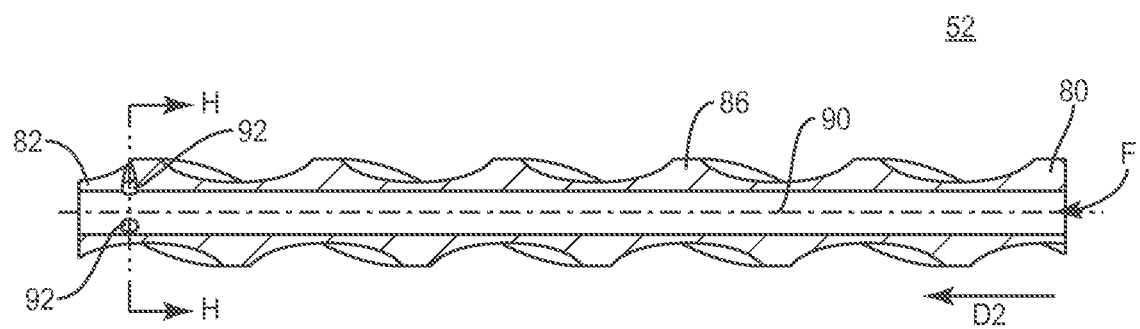
FIG. 18 is a cross section view of components of the system shown in FIG. 1.
Figure 19:
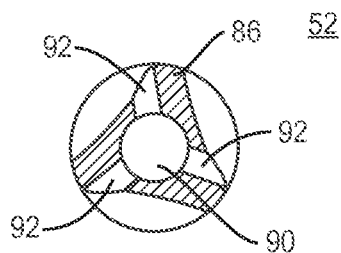
FIG. 19 is a cross section view taken along lines H-H shown in FIG. 18.
Figure 20:
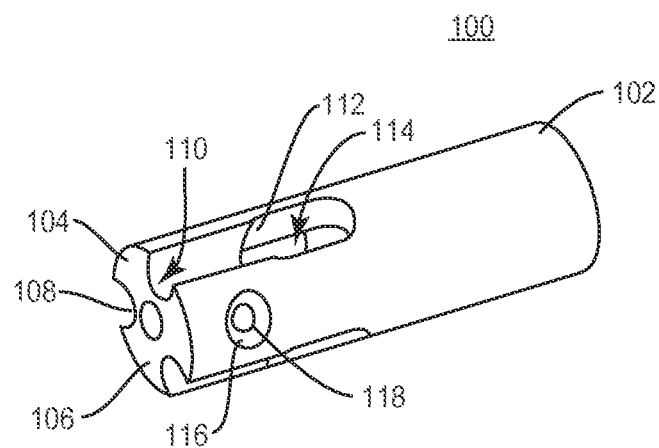
FIG. 20 is a perspective view of components of the system shown in FIG. 1.
Figure 21:
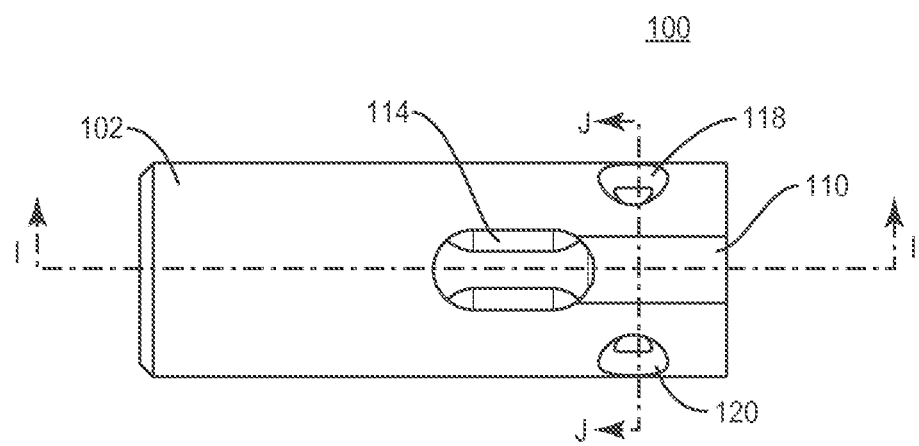
FIG. 21 is a side view of the components shown in FIG. 20.
Figure 22:
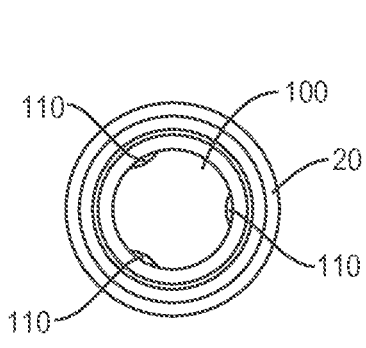
FIG. 22 is an end view of the components shown in FIG. 20.
Figure 23:
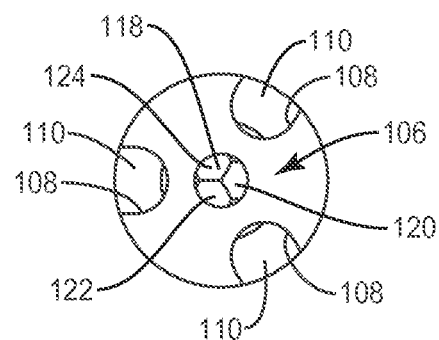
FIG. 23 is an end view of the components shown in FIG. 20.
Figure 24:
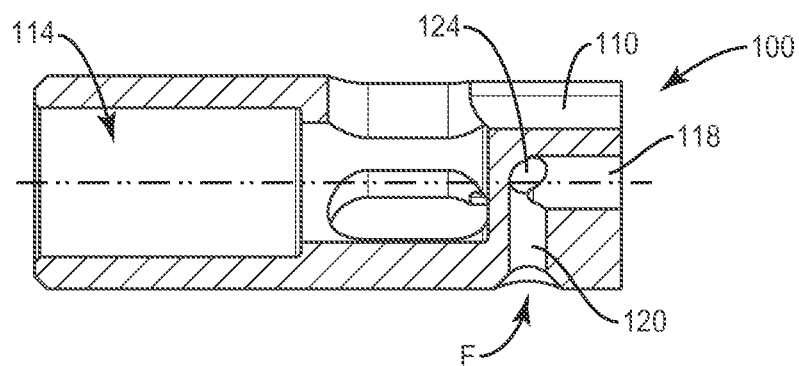
FIG. 24 is a cross section view taken along lines I-I shown in FIG. 21.
Figure 25:
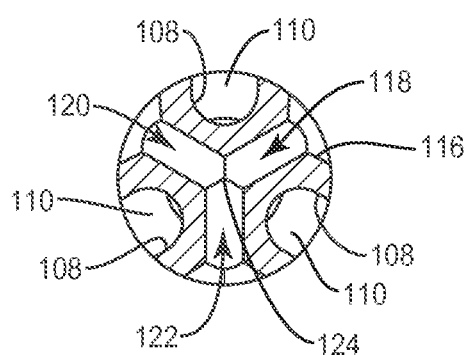
FIG. 25 is a cross section view taken along lines J-J shown in FIG. 21.

In one embodiment, as shown in FIGS. 27-32, system 10, similar to the systems and methods described herein, includes surgical instrument 12 having a grinder 200, similar to grinder 100 described herein. Grinder 200 extends between an end 202 and an end 204. End 204 is configured for disposal in portion 67 of cutter 50 (FIG. 9). Grinder 200 includes a surface 206 that defines arcuate cutting blades 208, similar to blades 108 described herein, configured to cut, shear and/or macerate cut tissue from transfer channel 88 (FIG. 3) into a smaller particle size for removal from a surgical site. Cutting blades 208 form opening 210, similar to openings 110 described herein. Grinder 200 includes a debris reservoir 214. Opening 210 is in communication with debris reservoir 214 such that the tissue that passes through opening 210 is transferred and/or conveyed into debris reservoir 214 for removal by a vacuum source attached with housing 20 (FIG. 1).

Grinder 200 includes a channel 218, similar to channels 118, 120, 122 described herein, which facilitates the flow of fluid F through grinder 200 into passageway 90. Channel 218 is configured for alignment with holes 72 during rotation of cutter 50 to receive fluid F. Channel 218 is configured to receive fluid F from holes 72 and direct fluid F into passageway 90 of shaft 52, as described herein, to direct fluid F in direction D2 into passageway 90.

Grinder 200 is configured for rotation relative to shaft 52 between an open, fluid communication position such that opening 210 is aligned with transfer channel 88 to facilitate passage of cut tissue from transfer channel 88 to debris reservoir 214 and a partially closed position such that surface 206 at least partially prevents passage of cut tissue from transfer channel 88 into debris reservoir 214. As grinder 200 rotates between the open and closed positions of opening 210, blades 208 cut, shear and/or macerate cut tissue from transfer channel 88 into a smaller particle size for removal from a surgical site. Cut tissue is transferred and/or conveyed with fluid F in direction D1.

The irrigation port is configured to deliver fluid F into surgical instrument 12, through holes 72, through channel 218 and into passageway 90. The force of fluid F directs cut tissue through transfer channel 88 to grinder 200. Fluid F mixed with tissue is transferred into debris reservoir 214 for removal via the vacuum source connected with surgical instrument 12.

Figure 33:
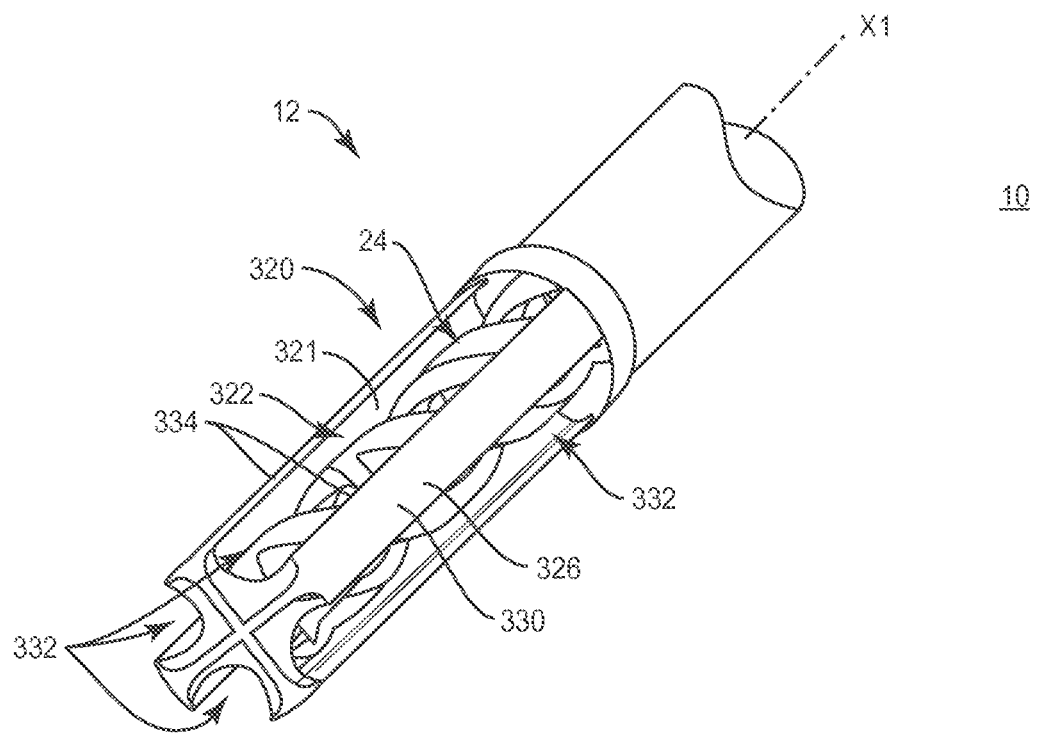
FIG. 33 is a perspective view of components of one embodiment of a surgical system in accordance with the principles of the present disclosure.
Figure 34:
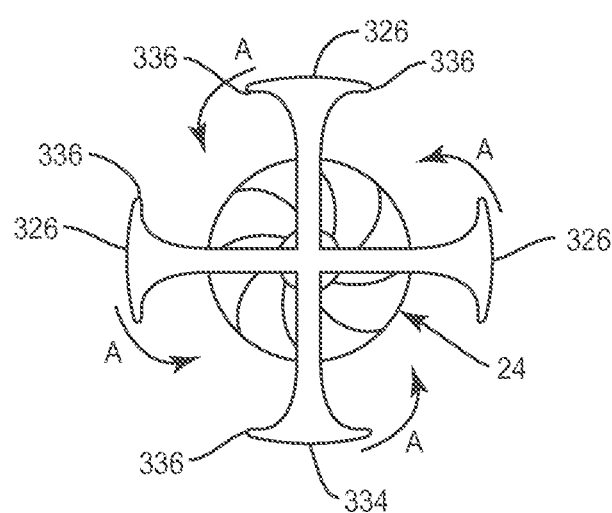
FIG. 34 is an end view of the components shown in FIG. 33.

In one embodiment, as shown in FIGS. 33 and 34, system 10, similar to the systems and methods described herein, includes surgical instrument 12 having a housing 320, similar to housing 20 described herein. Housing 320 includes an inner surface 321 that defines a channel 322 configured for disposal of auger 24, as described herein.

Housing 320 includes a wall 326 disposed about auger 24. Wall 326 includes a thickness and a surface 330. Surface 330 defines four spaced openings 332 extending through the thickness of wall 326. Wall 326 includes four spaced sections that comprise a cruciate cross section configuration. The sections are spaced 90 degrees apart and extend linearly to cutting surfaces 334, similar to surfaces 34 described herein, and are disposed about openings 332. Cutting surfaces 334 include blades 336, similar to blades 36 described herein. Blades 336 are configured to disrupt, scrape, cut and/or remove tissue from a surgical site. Manipulation including rotation, translation and/or angulation of housing 320 causes blades 336 to disrupt, scrape, cut and/or remove tissue at a surgical site and guide tissue into channel 322, in the direction shown by arrows A in FIG. 34.

Figure 35:
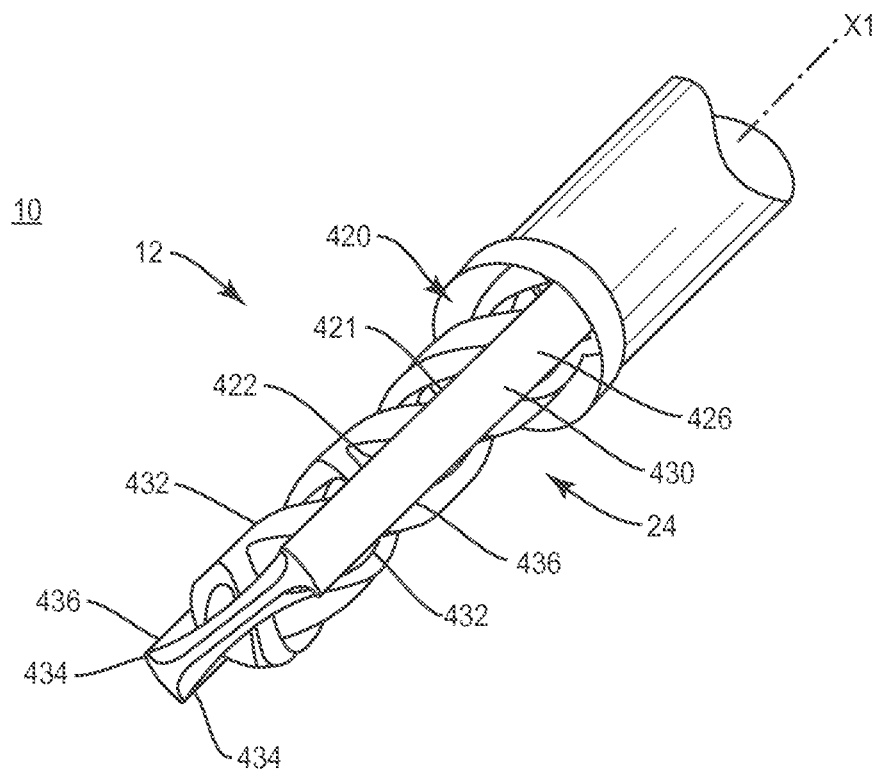
FIG. 35 is a perspective view of components of one embodiment of a surgical system in accordance with the principles of the present disclosure.
Figure 36:
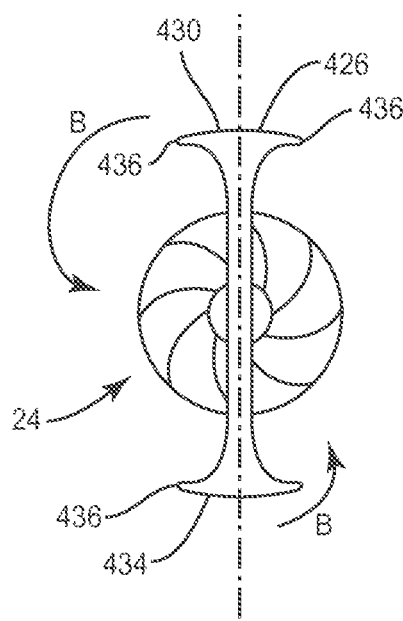
FIG. 36 is an end view of the components shown in FIG. 35.

In one embodiment, as shown in FIGS. 35 and 36, system 10, similar to the systems and methods described herein, includes surgical instrument 12 having a housing 420, similar to housing 20 described herein. Housing 420 includes an inner surface 421 that defines a channel 422 configured for disposal of auger 24, as described herein.

Housing 420 includes a wall 426 disposed about auger 24. Wall 426 includes a thickness and a surface 430. Surface 430 defines two spaced openings 432 extending through the thickness of wall 426. Wall 426 includes two spaced sections that are disposed in alignment and/or co-axial along an axis transverse to axis X1. The sections are spaced 180 degrees apart and extend linearly to cutting surfaces 434, similar to surfaces 34 described herein, and are disposed about openings 432. Cutting surfaces 434 include blades 436, similar to blades 36 described herein. Blades 436 are configured to disrupt, scrape, cut and/or remove tissue from a surgical site. Manipulation including rotation, translation and/or angulation of housing 420 causes blades 436 to disrupt, scrape, cut and/or remove tissue at a surgical site and guide tissue into channel 422, in the direction shown by arrows B in FIG. 36.

Figure 38:
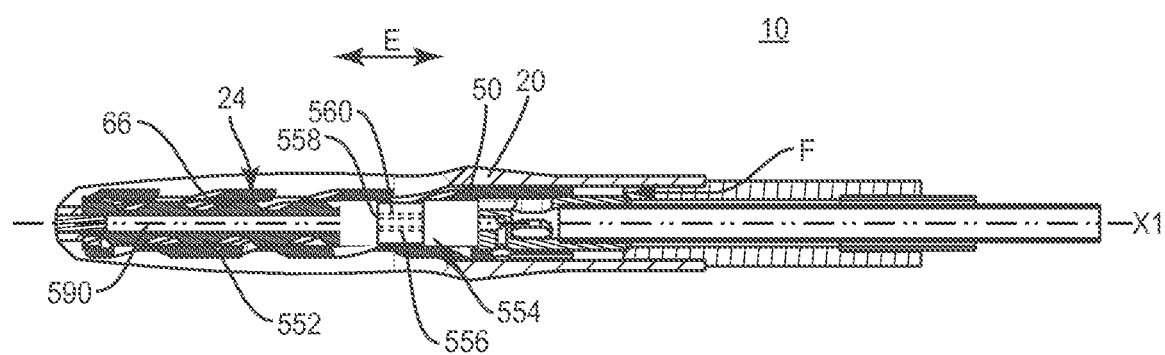
FIG. 38 is a cross section view of components of one embodiment of a surgical system in accordance with the principles of the present disclosure.
Figure 39:
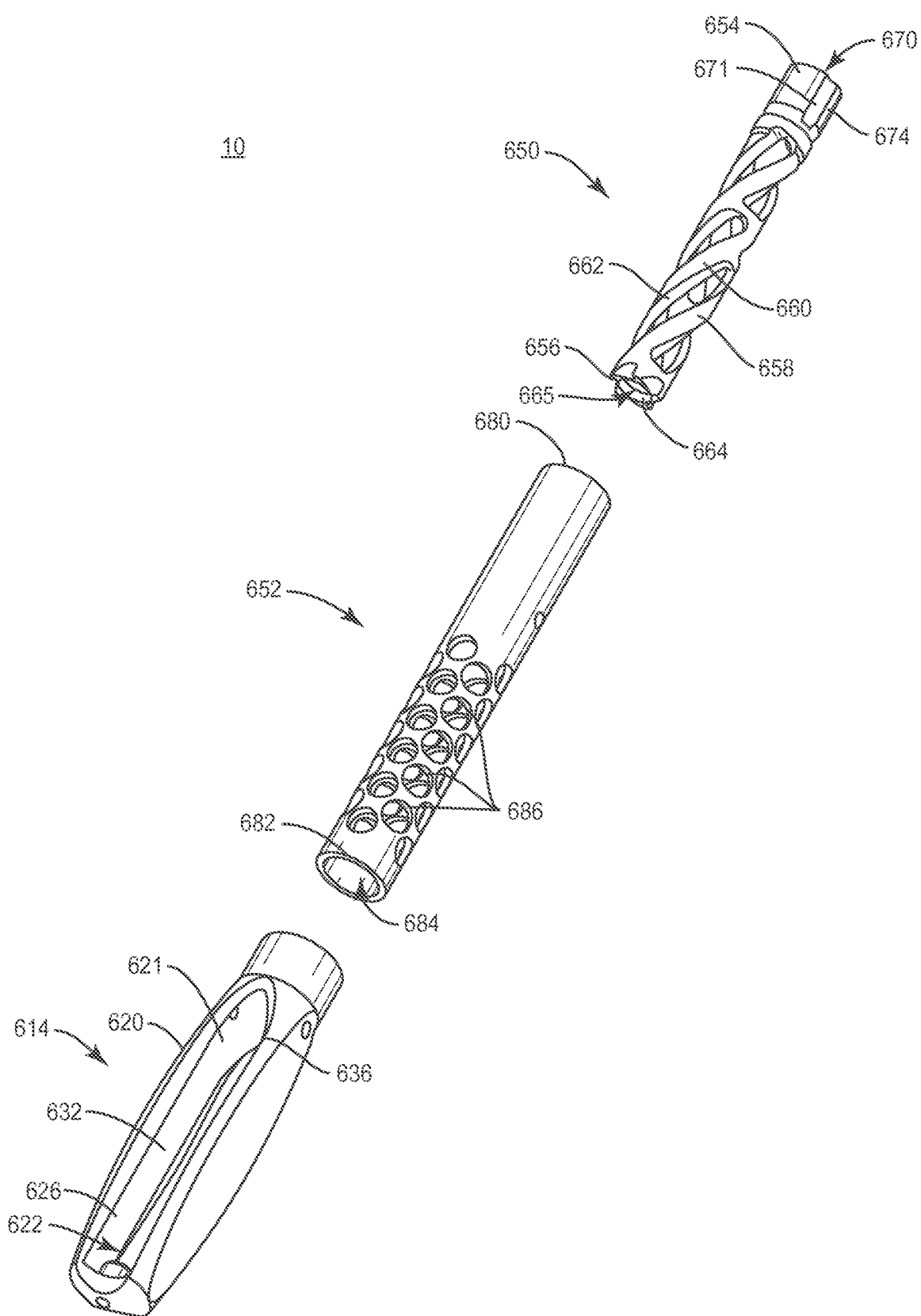
FIG. 39 is a perspective view of components of one embodiment of a surgical system in accordance with the principles of the present disclosure with parts separated.
Figure 40:
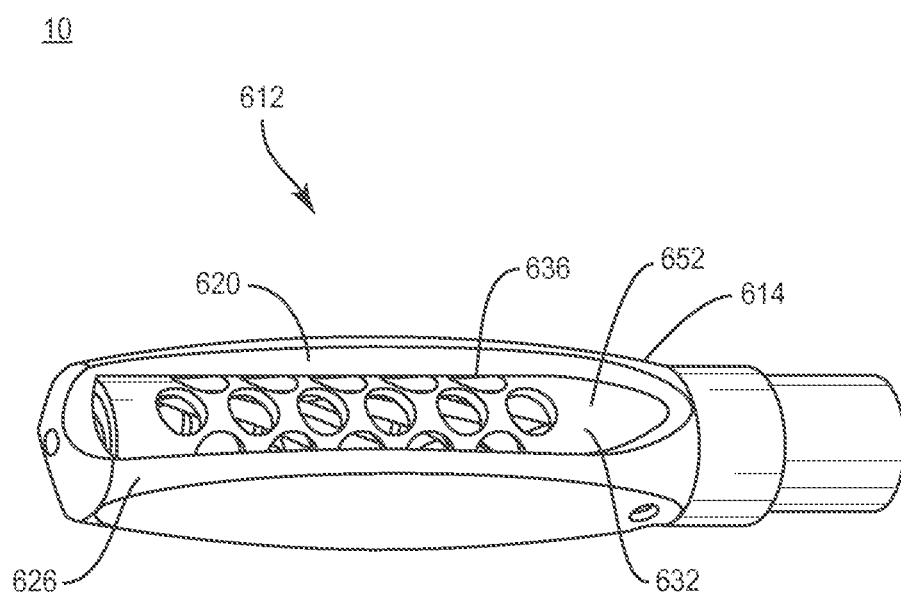
FIG. 40 is a perspective view of components of the system shown in FIG. 39.

In one embodiment, as shown in FIG. 38, system 10, similar to the systems and methods described herein, includes surgical instrument 12 having a stationary shaft 552, similar to stationary shaft 52 described herein. Shaft 552 is disposed within cavity 66 and has a reduced length such that cutter 50 and shaft 552 define a cavity portion 554 of cavity 66.

A piston 556 is configured for disposal with cavity portion 554. Piston 556 is configured for translation within cavity portion 554 along axis X1, in the directions shown by arrows E, to compact cut tissue, as described herein. In some embodiments, piston 556 includes a surface 558 that defines openings 560. Openings 560 are configured to provide a passageway for fluid flow F into a passageway 590, similar to passageway 90 described herein, and facilitate axial translation of piston 556 relative to cutter 50. As fluid flow F passes through passageway 590 and openings 560, piston 556 translates, in the directions shown by arrows E. Piston 556 translates relative to cutter 50 to move tissue debris, as described herein. In some embodiments, piston 556 comprises a compactor to engage and move tissue debris for removal of the tissue debris from auger 24. The dynamic fluid transfer and/or shear force created by rotation of cutter 50, similar to that described herein, directs fluid flow F and cut tissue into cavity 554 such that piston 556 compacts the cut tissue and directs the cut tissue into a grinder, similar to the grinders described herein, to facilitate grinding and cutting of tissue.

In one embodiment, as shown in FIGS. 39-42, system 10, similar to the systems and methods described herein, includes a surgical instrument 612, similar to surgical instrument 12 described herein. Surgical instrument 612 includes a member, such as, for example, a body 614, similar to body 14 described herein, which defines an axis X2 and includes a housing 620, similar to housing 20 described herein. Housing 620 includes an inner surface 621 that defines a channel 622. Channel 622 is configured for disposal of a member, such as, for example, an auger 624, as described herein.

Housing 620 includes a wall 626 disposed about auger 624. Wall 626 defines spaced openings 632 and includes blades 636, similar to blades 36 described herein. Manipulation including rotation, translation and/or angulation of housing 620 causes blades 636 to disrupt, scrape, cut and/or remove tissue at a surgical site and guide tissue into channel 622.

Auger 624, similar to auger 24 described herein, is configured for disposal in channel 622. Auger 624 includes a member, such as, for example, a rotatable cutter 650 and a member, such as, for example, a stationary shaft 652. Shaft 652 extends between an end 680 and an end 682 along axis X2 when disposed in housing 620. Shaft 652 is tubular and configured for disposal with channel 622. Shaft 652 is fixedly attached with housing 620 adjacent end 680 and/or end 682 to resist and/or prevent relative rotation therebetween. In some embodiments, shaft 652 may have cross section configurations, such as, for example, oval, cylindrical, triangular, square, polygonal, irregular, uniform, non-uniform, offset, staggered, undulating, arcuate, variable and/or tapered. Shaft 652 includes a wall surface that defines a channel 684 and a plurality of openings 686 that are circumferentially disposed about the wall surface. Openings 686 receive cut tissue, as described herein, adjacent openings 632 and facilitate, direct, transfer and/or convey the cut tissue to cutter 650.

Cutter 650 extends between an end 654 and an end 656. Cutter 650 extends along axis X2 when disposed in channel 684. Cutter 650 is tubular and configured for disposal within channel 684. In some embodiments, cutter 650 is connected with housing 620 via a flange 674 that facilities rotation of cutter 650 relative to housing 620. In some embodiments, cutter 650 may have cross section configurations, such as, for example, oval, cylindrical, triangular, square, polygonal, irregular, uniform, non-uniform, offset, staggered, undulating, arcuate, variable and/or tapered.

Cutter 650 includes a surface 658 that defines a plurality of spaced cutting flutes 660. Cutting flutes 660 are spaced along cutter 650 and form helical blades 662, similar to blades 62 described herein, extending along a length of cutter 650. Blades 662 are configured for rotation within housing 620 and within shaft 652 to disrupt, scrape, cut, shear and/or macerate tissue and/or transfer and/or convey tissue along shaft 652, as described herein.

Figure 41:
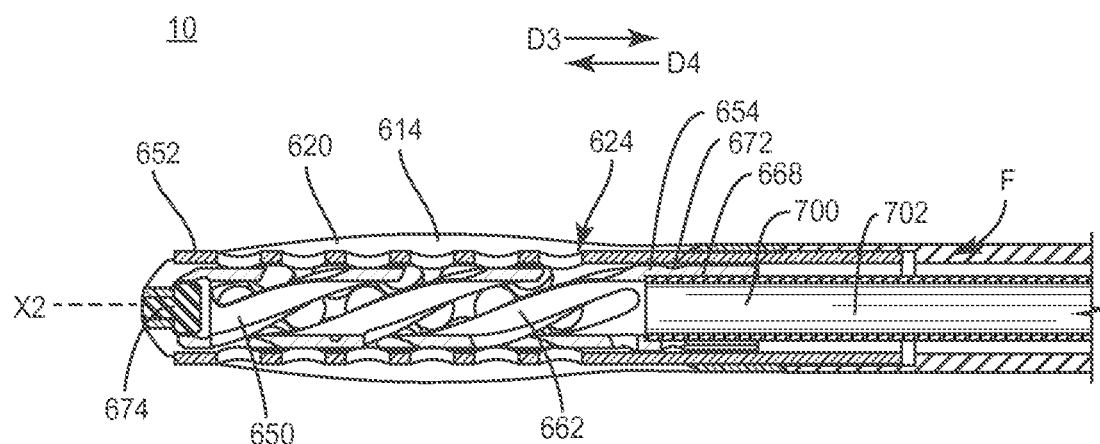
FIG. 41 is a cross section view of components of the system shown in FIG. 39.
Figure 42:
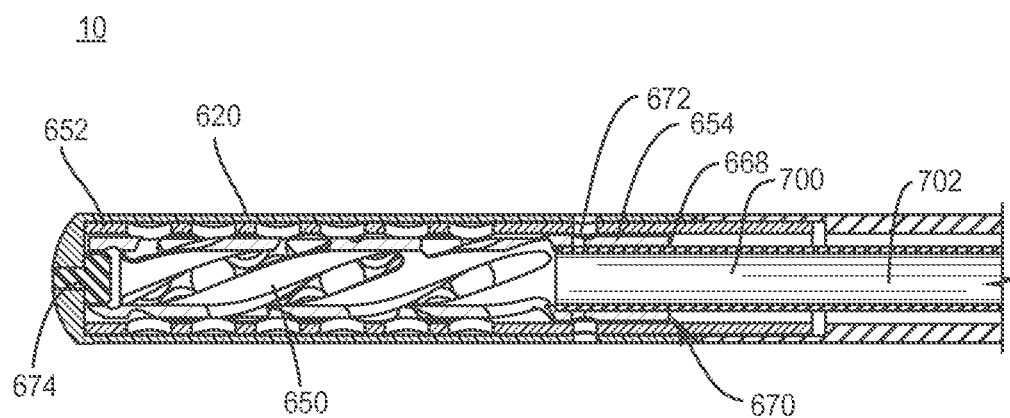
FIG. 42 is a cross section view of components of the system shown in FIG. 39.

Cutter 650 includes an inner surface 664 that defines an interior cavity 665. Cutter 650 is configured for rotation relative to shaft 652 to transfer tissue in a direction D3 along axis X2, as shown in FIG. 41. In some embodiments, blades 662 rotate relative to shaft 652 within housing 620 to disrupt, scrape, cut, shear and/or macerate cut tissue from blades 636 into a smaller particle size for removal a surgical site. In some embodiments, blades 662 rotate such that tissue disposed adjacent and/or between cutter 650 and shaft 652, and/or within cavity 665, is transferred and/or conveyed in direction D3 due to fluid transfer forces created between the helical configuration and rotation of cutter 650 relative to shaft 652 and/or housing 620. The tissue is transferred and/or conveyed towards a member, such as, for example, a cannula 700 for removal from a surgical site, similar to the systems and methods described herein.

Cannula 700 defines a transfer channel 702 that receives cut tissue from cavity 665 and directs the cut tissue in direction D3 along axis X2 for removal from a surgical site. In some embodiments, a vacuum source is connected to cannula 700 to direct fluid flow and cut tissue into transfer channel 702 and for removal from a surgical site. In some embodiments, a dynamic fluid transfer and/or shear force created by rotation of cutter 650 relative to shaft 652 directs fluid flow and cut tissue into transfer channel 702. End 654 includes a wall surface 668 that defines an opening 670 configured for disposal of a portion of cannula 700.

In some embodiments, fluid F flows through irrigation holes 672, which are in communication with fluid F supplied from an irrigation port, as described herein, for transfer of fluid F in a direction D4, as shown in FIG. 41. In some embodiments, holes 672 are configured to direct fluid F into channel 622, channel 684 and/or cavity 665, similar to that described herein. In some embodiments, surface 668 includes one or more grooves 671, which are in communication with a fluid F supplied from an irrigation port. In some embodiments, fluid F provides a hydraulic bearing surface between shaft 652, cutter 650 and/or housing 620 to facilitate rotation of cutter 650 and prevent wear, overheating and/or damage during operation of the components of surgical instrument 612.

An irrigation port is connected with components of surgical instrument 612 to deliver fluid F into surgical instrument 612, through holes 672 and into cavity 665, as described herein. In some embodiments, rotation of cutter 650 and the force of fluid flow F directs cut tissue through cavity 665 to transfer channel 702. Fluid F mixed with tissue is transferred into transfer channel 702 for removal via the vacuum source connected with surgical instrument 612.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member extending along an axis between opposite proximal and distal end surfaces, the first member including a channel, a wall and a plurality of openings, the wall extending from the proximal end surface to the distal end surface, the openings extending through the distal end surface and a thickness of the wall;
   a second member disposed in the channel, the second member including a passageway configured for disposal of cut tissue; and
   a third member including a plurality of spaced cutting flutes, the third member being disposed in the passageway such that the third member is rotatable relative to the second member to transfer the cut tissue along the axis.

2. A surgical instrument as recited in claim 1, wherein the distal end surface extends perpendicular to the axis.

3. A surgical instrument as recited in claim 1, wherein the wall includes spaced apart sections extending linearly to cutting surfaces, the cutting surfaces each extending parallel to the axis along entire lengths of the cutting surfaces.

4. A surgical instrument as recited in claim 1, wherein the second member is fixed relative to the first member.

5. A surgical instrument as recited in claim 3, wherein the cutting surfaces are disposed about the openings.

6. A surgical instrument as recited in claim 1, wherein the wall includes spaced apart sections extending linearly to cutting surfaces, the spaced apart sections including two sections that are disposed in alignment along an axis that extends transverse to the axis defined by the first member.

7. A surgical instrument as recited in claim 1, wherein the wall includes spaced apart sections extending linearly to cutting surfaces, the spaced apart sections including two sections that are spaced 180 degrees apart.

8. A surgical instrument as recited in claim 1, wherein the plurality of openings comprises two spaced openings.

9. A surgical instrument as recited in claim 1, wherein the plurality of openings comprises four openings.

10. A surgical instrument as recited in claim 1, wherein the wall includes spaced apart sections extending linearly to cutting surfaces, the spaced apart sections including four sections that comprise a cruciate cross section configuration.

11. A surgical instrument as recited in claim 1, wherein the wall includes spaced apart sections extending linearly to cutting surface, the spaced apart sections including four sections that are spaced 90 degrees apart.

12. A surgical instrument as recited in claim 1, wherein the cutting flutes form helical blades.

13. A surgical instrument as recited in claim 1, further comprising a fourth member disposed within an interior cavity of the third member.

14. A surgical instrument as recited in claim 1, further comprising a fourth member disposed within an interior cavity of the third member such that a transfer channel of the fourth member is coaxial with the interior cavity.

15. A surgical instrument as recited in claim 1, further comprising:
   a fourth member disposed within an interior cavity of the third member; and
   a vacuum source connected with the fourth member.

16. A surgical instrument as recited in claim 1, wherein the third member comprises a groove and an irrigation hole that is in communication with an interior cavity of the third member and the groove.

17. A surgical instrument comprising:
   a housing extending along an axis between opposite proximal and distal end surfaces, the housing including a channel, a wall and a plurality of openings, the wall extending from the proximal end surface to the distal end surface, the openings extending through the distal end surface and a thickness of the wall; and an auger comprising:
- a shaft disposed in the channel, the shaft including a passageway configured for disposal of cut tissue, and
- a cutter including a plurality of spaced cutting flutes, the cutter being disposed in the passageway such that the cutter is rotatable relative to the shaft to transfer the cut tissue along the axis.

18. A surgical instrument as recited in claim 17, wherein the openings extend through a thickness of the wall, the wall including spaced apart sections extending linearly to cutting surfaces.

19. A surgical instrument as recited in claim 17, wherein the shaft is fixed relative to the housing.

20. A surgical instrument comprising:
- a first member extending along an axis between opposite proximal and distal end surfaces, the first member including a channel, a wall and a plurality of openings, the wall extending from the proximal end surface to the distal end surface, the openings extending through the distal end surface and a thickness of the wall, the wall including cutting surfaces;
- a second member disposed in the channel, the second member including a passageway configured for disposal of cut tissue; and
- a third member including a plurality of spaced cutting flutes, the third member being disposed in the passageway such that the third member is rotatable relative to the second member to transfer the cut tissue along the axis, the third member being disposed entirely within the passageway.

* * * * *